(12) United States Patent
Choi

(10) Patent No.: US 11,806,512 B2
(45) Date of Patent: Nov. 7, 2023

(54) NEEDLELESS PAIN-FREE INJECTION DEVICE

(71) Applicant: P-TECH Co., Ltd., Jeonju-si (KR)

(72) Inventor: Yo Sung Choi, Jeonju-si (KR)

(73) Assignee: P-TECH Co., Ltd., Jeonju-si (KR)

( * ) Notice: Subject to any disclaimer, the term of this patent is extended or adjusted under 35 U.S.C. 154(b) by 365 days.

(21) Appl. No.: 17/056,068

(22) PCT Filed: Apr. 10, 2019

(86) PCT No.: PCT/KR2019/004258
§ 371 (c)(1),
(2) Date: Nov. 17, 2020

(87) PCT Pub. No.: WO2019/240364
PCT Pub. Date: Dec. 19, 2019

(65) Prior Publication Data
US 2021/0213202 A1 Jul. 15, 2021

(30) Foreign Application Priority Data

Jun. 12, 2018 (KR) .................. 10-2018-0067645

(51) Int. Cl.
*A61M 5/30* (2006.01)

(52) U.S. Cl.
CPC ........... *A61M 5/30* (2013.01); *A61M 2205/42* (2013.01); *A61M 2240/00* (2013.01); *A61M 2250/00* (2013.01)

(58) Field of Classification Search
CPC .... A61M 5/30; A61M 5/2046; A61M 5/2053; A61M 5/31576; A61M 2205/42
See application file for complete search history.

(56) References Cited

U.S. PATENT DOCUMENTS 5,064,413 A * 11/1991 McKinnon ............... A61M 5/30
604/72
6,210,359 B1 * 4/2001 Patel ....................... A61M 5/30
604/68

(Continued)

FOREIGN PATENT DOCUMENTS

CN   104399155 A  *  3/2015  ............... A61D 7/00
JP   2003500118 A     1/2003

(Continued)

*Primary Examiner* — Nathan R Price
*Assistant Examiner* — Sarah Dympna Grasmeder
(74) *Attorney, Agent, or Firm* — YOU & IP, LLC

(57) ABSTRACT

A needleless pain-free injection device according to the present disclosure includes a valve body, a valve member provided in an internal space of the valve body and airtightly sliding along the valve body, a liquefied gas container communicating with the internal space of the valve body and detachably coupled, at one end thereof, to the valve body, an operating knob provided on the exposed end of the valve member, a cylinder body coupled to one side of the valve body and having an internal space, a piston member provided such that one end thereof slides in the internal space of the cylinder body and having a piston rod, an injection unit provided with an injection piston rod coupled to the piston rod, and a gas passage forming means for selectively establishing and blocking the communication of the valve body and the cylinder body with outside air.

3 Claims, 3 Drawing Sheets

(56) References Cited

U.S. PATENT DOCUMENTS

| | | | |
|---|---|---|---|
| 6,689,092 B2 | 2/2004 | Zierenberg et al. | |
| 6,932,789 B2 | 8/2005 | Zierenberg et al. | |
| 7,470,274 B2 | 12/2008 | Lebet | |
| 2005/0085767 A1 | 4/2005 | Menassa | |
| 2008/0208114 A1* | 8/2008 | Landau | A61M 5/30 |
| | | | 604/68 |
| 2009/0118741 A1 | 5/2009 | Lebet | |
| 2018/0154082 A1 | 6/2018 | Yoh et al. | |

FOREIGN PATENT DOCUMENTS

| | | | | |
|---|---|---|---|---|
| JP | 2005516739 A | | 6/2005 | |
| KR | 10-2001-0067582 A | | 7/2001 | |
| KR | 10-2005-0098932 A | | 10/2005 | |
| KR | 10-0777146 B1 | | 11/2007 | |
| KR | 20120103859 A | * | 9/2012 | A61M 5/30 |
| KR | 10-1838631 B1 | | 4/2018 | |
| WO | 2000071185 A2 | | 11/2000 | |
| WO | 2003068296 A2 | | 8/2003 | |

\* cited by examiner

NEEDLELESS PAIN-FREE INJECTION DEVICE

TECHNICAL FIELD

The present disclosure relates to a needleless pain-free injection device, and more particularly, to a needleless pain-free injection device capable of providing a pressing force sufficient to rapidly inject an injectable drug while significantly reducing noise generated when the injectable drug is instantaneously injected through pneumatic pressure, thereby minimizing the impact of noise on subjects such as infants. In particular, the needleless pain-free injection device can be very useful in treatment of animals such as little birds that may die due to impact noise.

BACKGROUND ART

In general, syringes are considered as tools used by nurses or doctors to inject medicine directly into patient's bodies.

FIG. 1 is a view illustrating a configuration of a typical syringe. As illustrated in FIG. 1, the typical syringe includes one injection needle 1, and is used to inject the medicine within a cylinder 3 into a patient by pressing a piston 2.

In some cases, users such as diabetics who need to receive injections several times a day have to receive injections from time to time even during recuperation at home rather than in a hospital. In this case, the use of a typical syringe (including only an outer cylinder with a needle fitted thereto and a push rod) is difficult for the users to directly inject medicine into their own bodies, as well as to receive injections.

In addition, if general patients want to receive injections by themselves or if children with extreme movement need to receive injections, there is considerable difficulty in delivering injections without excellent injection technology. Moreover, the use of a thick needle may cause pains when the needle penetrates the skin.

Meanwhile, in an effort to solve these problems, a syringe has been proposed in which a typical syringe is elastically inserted into a sleeve to perform instantaneous injection by spring elasticity or pneumatic pressure. Alternatively, there has been proposed a painless syringe that has a small hole (about 0.1 mm diameter), instead of an injection needle, at the tip of the syringe and applies pressure from the rear of the syringe, thereby enabling an injectable solution to penetrate into the skin.

However, such a conventional painless syringe, for example, a painless syringe that strikes a piston by the elastic repulsion of a spring should use a separate loading jig since the syringe requires a very large force to compress and load the spring for an instant strike. Hence, the painless syringe may be very inconvenient and time-consuming to use because the loading jig must be coupled every time during compression and loading and decoupled after the loading.

In addition, the above spring-type painless syringe may not be applied to the case of skin care required to inject a small amount of injectable solution multiple times, since the injectable solution is injected at a time when a bundle of strikers are exerted once. Moreover, the spring-type painless syringe generates a large strike sound when striking the spring, which may cause discomfort to subjects and in particular may lead to the death of animals such as baby birds that are very sensitive to sound.

On the other hand, as another example of the conventional painless syringe, a painless syringe that strikes a piston by the extrusion of air does not provide an extrusion force sufficient to strike the piston but generates a large strike sound due to the extrusion of compressed gas in an extrusion path, which may cause discomfort or the like.

DISCLOSURE

Technical Problem

Various embodiments are directed to a needleless pain-free injection device capable of providing a pressing force sufficient to rapidly inject an injectable drug while significantly reducing noise generated when the injectable drug is instantaneously injected through pneumatic pressure, thereby minimizing the impact of noise on subjects such as infants. In particular, the needleless pain-free injection device can be very useful in treatment of animals such as little birds that may die due to impact noise.

Technical Solution

In an embodiment, there is provided a needleless pain-free injection device that includes a valve body having an internal space in a longitudinal direction thereof, a valve member slidably provided in the internal space of the valve body, the valve member having a plurality of protruding parts formed on an outer circumference thereof to airtightly slide along an inner wall of the valve body, a liquefied gas container having one end detachably coupled to the valve body and configured to communicate with the internal space of the valve body, with a nozzle part open, the nozzle part being formed at the other end of the liquefied gas container, an operating knob provided at an end of the valve member exposed from the valve body, a cylinder body coupled to one side of the valve body and closed at one end thereof, the cylinder body having an internal space in a longitudinal direction thereof, a piston member slidably provided while one end thereof is in airtight contact with the internal space of the cylinder body and having a piston rod formed at the one end thereof, an injection unit detachably coupled to the cylinder body and having an injection piston rod coupled to the piston rod in a contact or fitting manner, and a gas passage forming means for selectively establishing and blocking communication of the internal space of the valve body and the internal space of the cylinder body with outside air, according to the filling of the internal spaces with gas discharged from the liquefied gas container and the pressing of the operating knob, so that the piston member moves forward and backward.

The valve body and the cylinder body may be covered by a housing and integrated with each other. The valve member may have an elongated groove with a predetermined length formed longitudinally toward the center from one end thereof. The other end of the valve member may extend outward from the valve body. Each of the protruding parts formed on the outer circumference of the valve member may include a plurality of first extension flanges protruding radially outward from the center thereof, a plurality of second extension flanges protruding radially outward from an end thereof facing the liquefied gas container, and sliding sealing members provided in mounting grooves, formed by the respective first and second extension flanges, to maintain airtightness while in slidable contact with an inner surface of the valve body.

The gas passage forming means may include a first communication hole for allowing the internal space of the valve body to communicate with outside air, a second communication hole formed in the valve member for allowing the internal space of the valve body to communicate with the elongated groove of the valve member, a first switching communication path formed at one side of valve body and configured to communicate with or block an internal space on one side of the valve body according to the sliding of the valve member, a second switching communication path formed at the other side of the valve body and configured to establish or block communication of an internal space on the other side of the valve body with the first communication hole according to the sliding of the valve member, an inlet communication path formed in the cylinder body for allowing the first switching communication path to communicate with an internal space on the other side of the cylinder body, and an outlet communication path formed in the cylinder body and the valve body for allowing the second switching communication path to communicate with an internal space on one side of the cylinder body.

The piston member may include the piston rod configured to slide while in contact with an inner wall of the cylinder body, a piston head extending from the piston rod, and a sliding sealing member provided on an outer circumference of the piston head to maintain airtightness while in slidable contact with an inner surface of the cylinder body. The injection unit may include a syringe having the injection piston rod, and a rod protection cap having a syringe coupling part configured such that one end thereof is coupled to the syringe and the other end thereof is detachably coupled to the cylinder body. The cylinder body and the rod protection cap may be coupled in a bayonet mounting manner.

The piston member may further include a cushion member provided at an edge of at least one of both surfaces of the piston head.

Advantageous Effects

According to the needleless pain-free injection device of the present disclosure, it is possible to provide a pressing force sufficient to rapidly inject an injectable drug while significantly reducing noise generated when the injectable drug is instantaneously injected through pneumatic pressure.

In addition, the needleless pain-free injection device of the present disclosure can minimize the impact of noise on subjects such as infants, and in particular can be very useful in treatment of animals such as little birds that may die due to impact noise.

Furthermore, the needleless pain-free injection device of the present disclosure is convenient to use, allows a drive source for striking to be efficiently available, and has improved utilization since it is useful in various applications such as skin care as well as human and animal medical care.

MODE FOR DISCLOSURE

Figure 1:
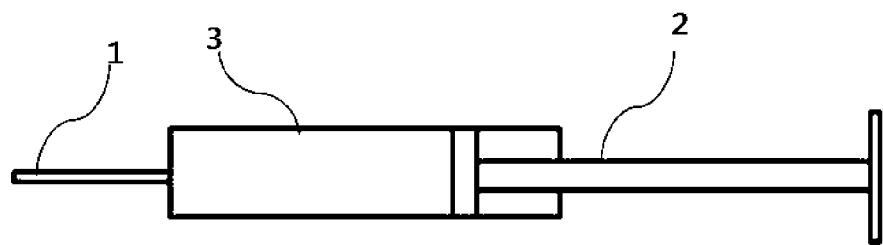
FIG. 1 is a view illustrating a configuration of a typical syringe.

The above and other objects, features and advantages of the present disclosure will be more clearly understood from the following detailed description taken in conjunction with the accompanying drawings.

Throughout the disclosure, like reference numerals refer to like parts throughout the accompanying drawings, and a redundant description thereof will be omitted. In certain embodiments, a detailed description of functions and configurations well known in the art may be omitted to avoid obscuring appreciation of the disclosure by a person of ordinary skill in the art.

Figure 2:
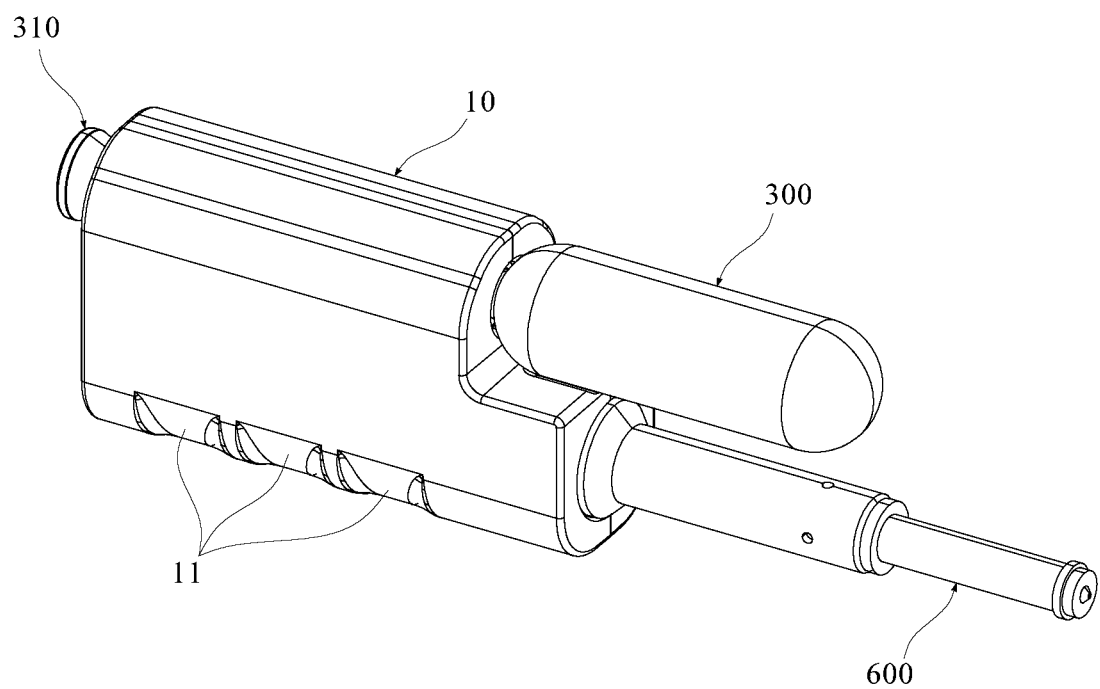
FIG. 2 is a perspective view illustrating a needleless pain-free injection device according to the present disclosure.
Figure 3:
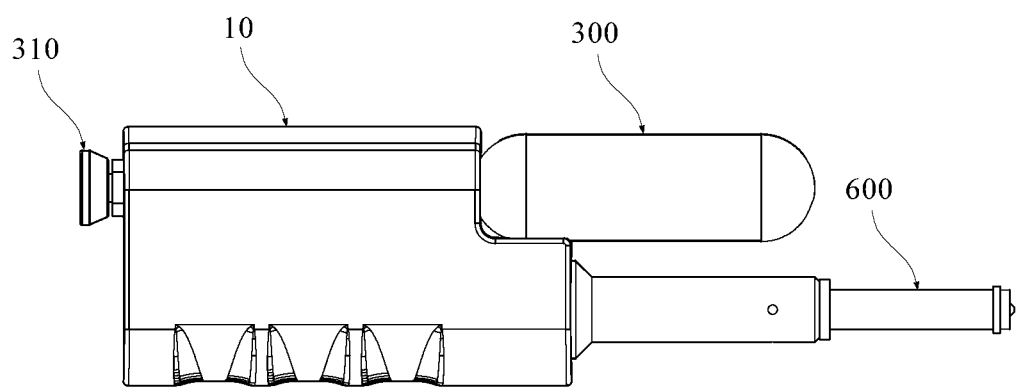
FIG. 3 is a side view illustrating the needleless pain-free injection device according to the present disclosure.
Figure 4:
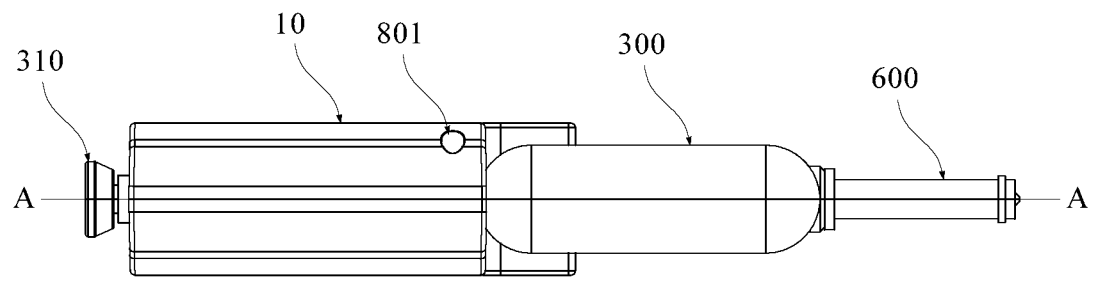
FIG. 4 is a top view illustrating the needleless pain-free injection device according to the present disclosure.
Figure 5:
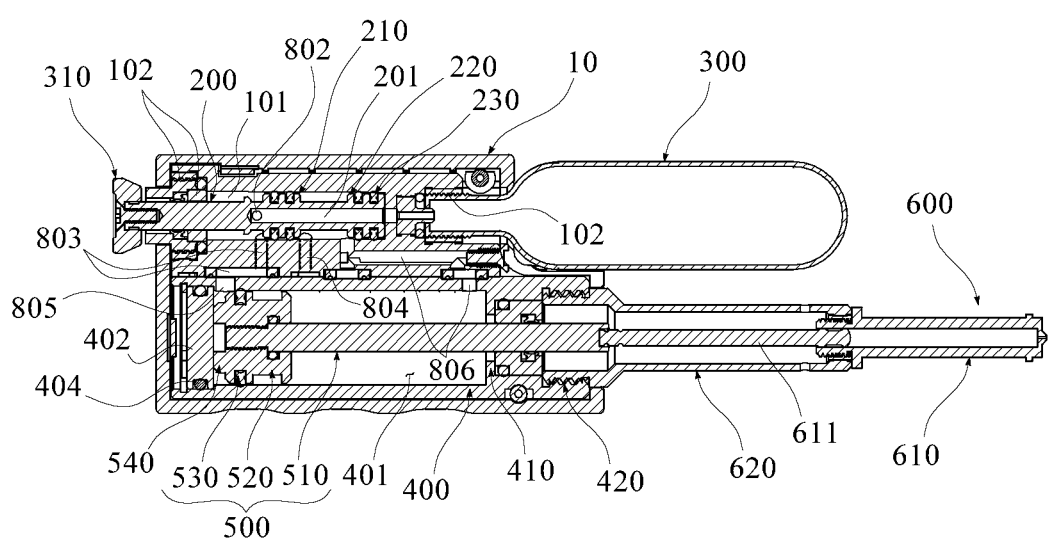
FIG. 5 is a cross-sectional view taken along line A-A of FIG. 4.

Hereafter, a needleless pain-free injection device according to an exemplary embodiment of the present disclosure will be described with reference to FIGS. 2 to 5. FIG. 2 is a perspective view illustrating the needleless pain-free injection device according to the present disclosure. FIG. 3 is a side view illustrating the needleless pain-free injection device according to the present disclosure. FIG. 4 is a top view illustrating the needleless pain-free injection device according to the present disclosure. FIG. 5 is a cross-sectional view taken along line A-A of FIG. 4. In the description of the configuration below, the terms "one end" or "one side" and "other end" or "other side" are used to distinguish between right and left based on the drawings, respectively. The term "one end" or "other end" is also used to represent each end.

As illustrated in FIGS. 2 to 5, the needleless pain-free injection device according to the present disclosure includes a valve body 100 having an internal space 101 in the longitudinal direction thereof. The needleless pain-free injection device includes a valve member 200 slidably provided in the internal space of the valve body 100, the valve member 200 has an elongated groove 201 with a predetermined length formed longitudinally toward the center from one end thereof and has the other end extending outward from the other end of the valve body 100, and the valve member 200 has a plurality of protruding parts formed on the outer circumference thereof to slide along the inner wall of the valve body 100. The needleless pain-free injection device includes a liquefied gas container 300 detachably coupled to one end of the valve body 100 and configured to communicate with the internal space of the valve body 100, with a nozzle part open, the nozzle part being formed at the other end of the liquefied gas container 300. The needleless pain-free injection device includes an operating knob 310 provided at the other end as an exposed end of the valve body 100. The needleless pain-free injection device includes a cylinder body 400 coupled to one side of the valve body 100 and closed at one end thereof, the cylinder body 400 having an internal space 401 in the longitudinal direction thereof. The needleless pain-free injection device includes a piston member 500 slidably provided while the other end thereof is in airtight contact with the internal space 401 of the cylinder body 400 and having a piston rod 510 formed at one end thereof. The needleless pain-free injection device includes an injection unit 600 detachably coupled to one end of the cylinder body 400 and having an injection piston rod 611 coupled to the piston rod 510 in a contact or fitting manner. The needleless pain-free injection device includes a gas passage forming means for selectively establishing and blocking the communication of the internal space 101 of the valve body 100 and the internal space 401 of the cylinder body 400 with the outside (outside air), according to the filling of the internal spaces with the gas discharged from the liquefied gas container 300 and the pressing of the operating knob 310, so that the piston member 500 moves forward and backward.

The valve body 100 and the cylinder body 400 are covered by a casing or housing 10 and integrated with each other.

Preferably, the casing or housing 10 has a plurality of gripping grooves 11 formed on one side thereof for easy gripping by a user. In the drawing, the gripping grooves 11 are illustrated as being formed on the lower side of the casing or housing 10.

The internal space (e.g., circular internal space) 101 of the valve body 100 is longer than the length of the valve member 200. The other end of the internal space 101 communicates with the outside, and a binding port 102 is formed at one end of the internal space 101 so that the nozzle part of the liquefied gas container 300 is detachably coupled to the binding port 102.

One end of the valve body 100 may be closed with a valve cap 103 that slidably supports one end of the valve member 200 at the center thereof.

The valve body 100 has a first communication hole 801 (see FIG. 4) for allowing the internal space 101 of the valve body 100 to communicate with the outside (outside air). The communication hole 801 formed in the valve body 100 is a constituent component of the gas passage forming means, and the communication relationship thereof will be described below in connection with the gas passage forming means.

The valve member 200 has a cylindrical body, and the elongated groove 201 with a predetermined length in the valve member 200 is formed toward the center from one end of the cylindrical body. The other end of the elongated groove 201 is closed.

Each of the protruding parts formed on the outer circumference of the valve member 200 includes a plurality of first extension flanges 210 protruding radially outward from the center thereof, a plurality of second extension flanges 220 protruding radially outward from one end thereof, and sliding sealing members (e.g., O-rings) 230 provided in mounting grooves formed by the respective first and second extension flanges 210 and 220 to maintain airtightness while in slidable contact with the inner surface of the valve body 100.

The valve member 200 has a second communication hole 802 for allowing the elongated groove 201 to communicate with the internal space 101 of the valve body 100, and the valve body 100 has an outer circumference space 803 defined in a predetermined portion thereof. The second communication hole 802 and the outer circumference space 803 are constituent components of the gas passage forming means, and the communication relationship thereof will be described in detail below in connection with the gas passage forming means.

The liquefied gas container 300 is filled with liquid-phase gas, for example, liquefied carbon dioxide ($CO_2$). In this state, when the nozzle part of the liquefied gas container 300 is opened at the same time as being coupled to the binding port 102 of the valve body 100, the gas in the liquefied gas container 300 may be discharged into the internal space 101 of the valve body 100 while vaporizing through the nozzle part of the liquefied gas container 300. Here, the above gas is not limited to carbon dioxide.

The nozzle part of the liquefied gas container 300 is configured such that the filled liquefied gas (e.g., liquefied carbon dioxide) may be discharged while vaporizing through the nozzle part at the same time as the nozzle part is coupled to the binding port 102 of the valve body 100. A detailed description thereof will be omitted.

The internal space 401 is defined at one side of the cylinder body 400. The cylinder body 400 has a guide partition wall 410 formed at the other side thereof. The guide partition wall 410 communicates with the internal space 401 and has a guide hole formed to airtightly guide the piston rod 510 of the piston member 500. The cylinder body 400 has a coupling part 420 formed at one end thereof so that a rod protection cap 620 of the injection unit 600, which will be described later, is detachably coupled to the coupling part 420.

A cylinder body cap 402 is coupled to and airtightly closes the other end of the cylinder body 400. The outer circumference of the cylinder body cap 402 is provided with an O-ring 403 which may serve to airtightly close the cylinder body 400.

The piston member 500 provided in the cylinder body 400 includes a piston rod 510 configured to airtightly slide along the guide hole in the guide partition wall 410 of the cylinder body 400, a piston head 520 formed at the other end of the piston rod 510 and in contact with the inner wall surface of the cylinder body 400, and a sliding sealing member (e.g., O-ring) 530 provided on the outer circumference of the piston head 520 to maintain airtightness while in slidable contact with the inner surface of the cylinder body 400.

The piston member 500 may further include a cushion member 540 provided at the edge of the rear surface (surface opposite to the side where the base of the piston rod 510 is formed) of the piston head 520. The cushion member 540 may also be provided on the front surface (surface of the side where the base of the piston rod 510 is formed) of the piston head 520 or on one surface of the guide partition wall 410 directed toward the piston head 520.

When the piston head 520 having a diameter relatively larger than the diameter of the piston rod 510 instantaneously slides with a strong force in the internal space 401 of the cylinder body 400, the cushion member 540 serves to prevent the piston head 520 from directly colliding with the cylinder body 400, thereby securing durability.

The injection unit 600 includes a syringe 610 having an injection piston rod 611, and a rod protection cap 620 having a syringe coupling part configured such that one end thereof is coupled to the syringe 610 and the other end thereof is detachably coupled to the coupling part 420 of the cylinder body 400.

The coupling between the coupling part 420 of the cylinder body 400 and the syringe coupling part of the rod protection cap 620 is not particularly limited as long as they can be detachably coupled to each other. For example, in order to facilitate the attachment and detachment between the cylinder body 400 and the injection unit 600, the coupling part 420 of the cylinder body 400 is of a cylindrical shape and the syringe coupling part is of a cylindrical shape. Thus, the syringe coupling part and the coupling part 420 may be coupled in a bayonet mounting manner in which the syringe coupling part is fitted to the outer circumference of the coupling part 420 and then locked thereto by rotation in one direction.

The gas passage forming means includes a first communication hole 801 for allowing the internal space 101 of the valve body 100 to communicate with the outside (outside air), a second communication hole 802 formed in the valve member 200 for allowing the internal space 101 of the valve body 100 to communicate with the elongated groove 201 of the valve member 200, a first switching communication path 803 formed at one side of valve body and configured to communicate with and block an internal space 101 on one side of the valve body 100 according to the sliding of the valve member 200, a second switching communication path 804 formed at the other side of the valve body 100 and configured to establish and block the communication of an internal space 101 on the other side of the valve body 100 with the first communication hole 801 according to the sliding of the valve member 200, an inlet communication path 805 for allowing the first switching communication path 803 to communicate with an internal space 401 on the other side (i.e., the other end of the piston head 520) of the cylinder body 400, and an outlet communication path 806 formed in the cylinder body 400 and the valve body 100 for allowing the second switching communication path 804 to communicate with an internal space 401 on one side (i.e., the piston rod 510 side) of the cylinder body 400.

As illustrated in FIG. 3, in the state in which the operating knob 310 is pressed so that the valve member 200 moves forward, the first switching communication path 803 communicates with the internal space 101 on the other side of the valve body 100 and with the internal space 401 on the other side of the cylinder body 400 through the inlet communication path 805. Thus, the piston member 500 moves forward to strike the injection piston rod 611 of the injection unit 600.

In this case, the first switching communication path 803 is airtightly separated from the second switching communication path 804 by the first extension flanges 210 of the valve member 200 provided with the sliding sealing members 230. The gas (air) in the inner space 401 on one side of the cylinder body 400 is discharged to the outside through the outlet communication path 806, through the first switching communication path 803, which communicates with the internal space 101 on one side of the valve body 100, through the second switching communication path 804, and through the first communication hole 801.

On the other hand, when the pressed operating knob 310 is released, the valve member 200 moves backward (direction opposite to the pressing direction) again by the force of the gas discharged from the liquefied gas container 300. Thus, the communication between the valve body 100 and the cylinder body 400 is blocked, which is in a standby state. At this time, the injection unit 600 is replaced and the standby state is maintained.

Specifically, the communication relationship of the gas passage forming means according to the forward and backward movement of the valve member 200 will be described.

In connection with the first and second communication holes 801 and 802, the first and second switching communication paths 803 and 804, and the inlet and outlet communication paths 805 and 806, the gas discharged from the liquefied gas container 300 is introduced into the internal space 101 of the valve body 100 while moving the valve member 200 backward (to the left on the drawing). Thus, the elongated groove 201 of the valve member 200 and the internal space 101 of the valve body 100 are filled with the gas. In this case, the internal space 101 of the valve body 100 and the first switching communication path 803 are blocked by the extension flanges (first extension flanges 210), which is in a standby state (loaded state).

In such a standby state, when the user presses the operating knob 310 so that the valve member 200 moves forward (to the right on the drawing), the internal space 101 of the valve body 100 communicates with the first switching communication path 803. Thus, the gas moves the piston member 500 by striking the piston head 520 through the inlet communication path 805, thereby allowing the injectable solution in the injection unit 600 to be discharged. In this case, the air (gas) present in the internal space 401 on the other side of the cylinder body 400 is discharged to the outside through the outlet communication path 806, the second switching communication path 804, and the first communication hole 801, which is in a strike state (injection state).

Then, when the user removes the force pressing the operating knob 310, it is returned back to the standby state (loaded state).

As described above, in the present disclosure, the gas passage forming means having the above configuration may allow the gas, which is discharged from the liquefied gas container 300 when the operating knob is operated, to be delivered to the cylinder body 400 at rapid and strong discharge pressure in the standby state (i.e., loaded state), thereby striking the piston member 500. Therefore, it is possible to instantaneously inject the injectable solution without generating noise.

Meanwhile, the needleless pain-free injection device of the present disclosure may further include a medicine injection control means for allowing the injectable solution in the injection unit 600 to be injected at a constant rate only for a very short period of time by controlling the sliding of the piston member 500 (e.g., constant-speed movement) when the piston member 500 is moved instantaneously (for a time less than 1 second) by the pressure of extruded vaporized gas (filling gas).

Although not illustrated in the drawings as an embodiment, the medicine injection control means includes a plurality of stopper grooves formed at intervals on the outer circumference of the piston rod 510 of the piston member 500 in the longitudinal direction thereof, a mounting hole formed on one side of the guide long hole of the cylinder body 400 in a direction orthogonal to the guide long hole, a spherical stopper linearly movably provided in the mounting hole, a cover cap coupled to cover the top of the mounting hole, and an elastic member (i.e., coil spring) provided between the spherical stopper and the cover cap to elastically support the spherical stopper.

In the medicine injection control means, the cover cap may be screwed to the mounting hole. Thus, it is possible to adjust the elastic force of the elastic member by turning the cover cap clockwise or counterclockwise. On the outer surface of the cover cap, a design elasticity indicator may be provided, which indicates the action of the elastic force of the elastic member according to the coupling pitch of the cover cap, based on the outer surface of the cylinder body coupled to the cover cap.

Accordingly, it is possible to adjust the elastic force of the elastic member and the pressing force of the spherical stopper to the piston rod by adjusting the coupling pitch of the cover cap.

Through the provision of the medicine injection control means configured to control the moving speed of the piston member, it is possible to reduce scars on the injection surface as well as noise and to relatively more relieve pains.

According to the needleless pain-free injection device of the present disclosure as described above, it is possible to provide the pressing force sufficient to rapidly inject the injectable drug while significantly reducing noise generated when the injectable drug is instantaneously injected through the pneumatic pressure. In addition, the needleless pain-free injection device can minimize the impact of noise on the subjects such as infants, and in particular can be very useful in the treatment of animals such as little birds that may die due to impact noise.

Furthermore, the needleless pain-free injection device of the present disclosure is convenient to use, allows a drive source for striking to be efficiently available, and has improved utilization since it is useful in various applications such as skin care as well as human and animal medical care.

The accompanying drawings as well as the embodiments described in the present specification are merely illustrative of some of the technical ideas included in the present disclosure. Accordingly, the embodiments disclosed herein are intended to illustrate, rather than to limit, the technical ideas of the present disclosure, and it is therefore obvious that the scope of the technical ideas of the present disclosure is not limited by these embodiments. Various modifications and specific embodiments that can be easily inferred by those skilled in the art within the scope of the technical ideas included in the specification and drawings of the present disclosure should be interpreted as falling within the scope of the present disclosure.

INDUSTRIAL APPLICABILITY

The present disclosure is applicable to the field of medical syringes and veterinary syringes.

The invention claimed is:

1. A needleless pain-free injection device comprising:
   a valve body having an internal space in a longitudinal direction of the valve body;
   a valve member slidably provided in the internal space of the valve body, the valve member having a plurality of protruding parts formed on an outer circumference of the valve member to airtightly slide along an inner wall of the valve body;
   a liquefied gas container detachably coupled to the valve body such that the liquefied gas container and the valve member are arranged on the same central axis, the liquefied gas container comprising a nozzle at an opening to communicate with the internal space of the valve body;
   an operating knob provided at an end of the valve member exposed from the valve body;
   a cylinder body coupled to one side of the valve body and closed at one end of the cylinder body, the cylinder body having an internal space in a longitudinal direction of the cylinder body;
   a piston member slidably provided in the internal space of the cylinder body and including
      a piston head configured to slide along an inner surface of the cylinder body,
      a piston rod extending from one side of the piston head, and
      a cushion member formed at the other side of the piston head to prevent the piston head from directly colliding with the cylinder body;
   an injection unit detachably coupled to the cylinder body and having an injection piston rod coupled to the piston rod in a contact or fitting manner;
   a first communication hole for allowing the internal space of the valve body to communicate with outside air;
   a second communication hole formed in the valve member for allowing the internal space of the valve body to communicate with an elongated groove of the valve member;
   a first switching communication path formed at a first side of the valve body and configured to communicate with or block an internal space on the first side of the valve body according to the sliding of the valve member;
   a second switching communication path formed at a second side of the valve body and configured to establish or block communication of an internal space on the second side of the valve body with the first communication hole according to the sliding of the valve member;
   an inlet communication path formed in the cylinder body for allowing the first switching communication path to communicate with a first internal space of the cylinder body, the first internal space of the cylinder body being a space between a cylinder body cap and the piston head,
   an outlet communication path formed in the cylinder body and the valve body for allowing the second switching communication path to communicate with a second internal space of the cylinder body, the second internal space of the cylinder body being a space between the piston head and a guide partition wall,
   wherein when the valve member moves forward, a gas discharged from the liquified gas container moves through, in sequence, the second communication hole, the internal space of the valve body, the first switching communication path, the inlet communication path, and the first internal space of the cylinder body, to strike the piston head, thereby moving forward the piston member.

2. The needleless pain-free injection device according to claim 1, wherein:
   the valve body and the cylinder body are covered by a housing and integrated with each other, the valve member has the elongated groove with a predetermined length formed longitudinally toward the center from one end thereof, and the other end of the valve member extends outward from the valve body; and
   each of the protruding parts formed on the outer circumference of the valve member comprises a plurality of first extension flanges protruding radially outward from the center thereof, a plurality of second extension flanges protruding radially outward from an end thereof facing the liquefied gas container, and sliding sealing members provided in mounting grooves, formed by the respective first and second extension flanges, to maintain airtightness while in slidable contact with the inner wall of the valve body.

3. The needleless pain-free injection device according to claim 1, wherein:
   the piston member further comprises a sliding sealing member provided on an outer circumference of the piston head to maintain airtightness while in slidable contact with the inner surface of the cylinder body;
   the injection unit comprises a syringe having the injection piston rod, and a rod protection cap having a syringe coupling part configured such that one end thereof is coupled to the syringe and the other end thereof is detachably coupled to the cylinder body; and
   the cylinder body and the rod protection cap are coupled in a bayonet mounting manner.

* * * * *